(12) United States Patent
James et al.

(10) Patent No.: US 11,783,225 B2
(45) Date of Patent: Oct. 10, 2023

(54) LABEL-BASED INFORMATION DEFICIENCY PROCESSING

(71) Applicant: Optum, Inc., Minnetonka, MN (US)

(72) Inventors: Donald W. James, Costa Mesa, CA (US); Kathrin Bujna, Dublin (IE); Daniel J. Mulcahy, Cambridge, MA (US)

(73) Assignee: OPTUM, INC., Minnetonka, MN (US)

( * ) Notice: Subject to any disclaimer, the term of this patent is extended or adjusted under 35 U.S.C. 154(b) by 921 days.

(21) Appl. No.: 16/747,686

(22) Filed: Jan. 21, 2020

(65) Prior Publication Data

US 2021/0011904 A1 Jan. 14, 2021

Related U.S. Application Data

(60) Provisional application No. 62/872,858, filed on Jul. 11, 2019.

(51) Int. Cl.
*G06N 5/02* (2023.01)
*G06N 7/00* (2023.01)
(Continued)

(52) U.S. Cl.
CPC ............... *G06N 20/00* (2019.01); *G06N 3/04* (2013.01); *G06N 3/08* (2013.01); *G06N 5/02* (2013.01); *G06N 7/01* (2023.01); *G16H 10/60* (2018.01)

(58) Field of Classification Search
CPC ........... G06N 5/02; G06N 7/005; G16H 10/60
See application file for complete search history.

(56) References Cited

U.S. PATENT DOCUMENTS

2013/0262357 A1 10/2013 Amarasingham et al.
2014/0108047 A1\* 4/2014 Kinney .................. G16H 10/60
705/3
(Continued)

FOREIGN PATENT DOCUMENTS

CN 110134946 A \* 8/2019

OTHER PUBLICATIONS

Ma, Fenglong, et al. "Dipole: Diagnosis prediction in healthcare via attention-based bidirectional recurrent neural networks." Proceedings of the 23rd ACM SIGKDD international conference on knowledge discovery and data mining. 2017. (Year: 2017).\*
(Continued)

*Primary Examiner* — Hal Schnee
(74) *Attorney, Agent, or Firm* — Alston & Bird LLP

(57) ABSTRACT

There is a need for more effective and efficient information deficiency processing. This need can be addressed by, for example, solutions for performing/executing label-based information deficiency processing. In one example, a method includes receiving a predictive input associated with a predictive entity based on the predictive input; determining a plurality of encoding probability values for the predictive entity based on the predictive input; determining a plurality of attention-based encoding vectors for the predictive entity based on the plurality of encoding probability values; determining an encoding deficiency prediction for the predictive entity, wherein the encoding deficiency prediction indicates a deficient subset of a plurality of encoding designations; and for each encoding designation in the deficient subset, performing a corresponding prediction-based action.

20 Claims, 14 Drawing Sheets

(51) Int. Cl.
*G16H 10/60* (2018.01)
*G06N 20/00* (2019.01)
*G06N 3/08* (2023.01)
*G06N 3/04* (2023.01)
*G06N 7/01* (2023.01)

(56) References Cited

U.S. PATENT DOCUMENTS

| | | |
|---|---|---|
| 2015/0106123 A1 | 4/2015 | Amarasingham et al. |
| 2015/0235001 A1 | 8/2015 | Fouts |
| 2016/0012187 A1* | 1/2016 | Zasowski ............... G06Q 10/10 705/3 |
| 2017/0235884 A1* | 8/2017 | Harmon ................. G16H 40/20 705/2 |
| 2018/0039738 A1 | 2/2018 | Lateef et al. |
| 2018/0341875 A1 | 11/2018 | Carr |
| 2019/0311800 A1* | 10/2019 | Patel ....................... G16H 40/40 |
| 2020/0027567 A1* | 1/2020 | Xie ......................... G16H 70/60 |
| 2020/0226321 A1* | 7/2020 | Burns ..................... G16H 10/60 |
| 2021/0098135 A1* | 4/2021 | Frings .................... G16H 50/70 |

OTHER PUBLICATIONS

Qiao, Zhi, et al. "Mnn: multimodal attentional neural networks for diagnosis prediction." Extraction 1 (2019): A1. (Year: 2019).*
Shi, Haoran, et al. "Towards automated ICD coding using deep learning." arXiv preprint arXiv:1711.04075 (2017). (Year: 2017).*
Kamath, Uday, John Liu, and James Whitaker. "Convolutional neural networks." Deep learning for NLP and speech recognition. Springer, Cham, 2019. 263-314. (Year: 2019).*

* cited by examiner

1400

She presents with COPD. It is described as chest tighten... The complaint moderately limits activities. The severity... actions include inhaled anticholingerics, inhaled steroids ...

FIG. 14

LABEL-BASED INFORMATION DEFICIENCY PROCESSING

CROSS-REFERENCE TO RELATED APPLICATIONS

The present application claims the benefit of U.S. Provisional Patent Application No. 62/872,858, filed Jul. 11, 2019, which is incorporated herein in its entirety.

BACKGROUND

Various embodiments of the present invention address technical challenges related to performing information deficiency processing. Various embodiments of the present address the shortcomings of existing information deficiency processing systems and disclose various techniques for efficiently and reliably performing information deficiency processing.

BRIEF SUMMARY

In general, embodiments of the present invention provide methods, apparatus, systems, computing devices, computing entities, and/or the like for performing/executing label-based information deficiency processing. Certain embodiments utilize systems, methods, and computer program products that perform/execute anomaly detection using one or more of encoding probability values, attention-based encoding vectors, encoding deficiency predictions, deficiency utility values, encoding machine learning models, and attention-based machine learning models.

In accordance with one aspect, a method is provided. In one embodiment, the method comprises: receiving a predictive input associated with a predictive entity; determining, based at least in part on the predictive input, a plurality of encoding probability values for the predictive input, wherein each encoding probability value of the plurality of encoding probability values indicates an estimated encoding association of the predictive input with a corresponding encoding designation of a plurality of encoding designations; determining, based at least in part on the predictive input, a plurality of attention-based encoding vectors for the predictive input, wherein each attention-based encoding vector of the plurality of attention-based encoding vectors relates a corresponding encoding designation of the plurality of encoding designations to a related subset of the predictive input; determining, based at least in part on the plurality of encoding probability values, predictive entity data associated with the predictive entity, and deficiency utility data associated with the plurality of encoding designations, an encoding deficiency prediction for the predictive input, wherein the encoding deficiency prediction indicates a deficient subset of the plurality of encoding designations as well as a deficiency utility value for each encoding designation in the deficient subset; and for each encoding designation in the deficient subset, performing a corresponding prediction-based action based at least in part on the deficiency utility value for the encoding designation and the attention-based encoding vector for the encoding designation.

In accordance with another aspect, a computer program product is provided. The computer program product may comprise at least one computer-readable storage medium having computer-readable program code portions stored therein, the computer-readable program code portions comprising executable portions configured to: receive a predictive input associated with a predictive entity; determine, based at least in part on the predictive input, a plurality of encoding probability values for the predictive input, wherein each encoding probability value of the plurality of encoding probability values indicates an estimated encoding association of the predictive input with a corresponding encoding designation of a plurality of encoding designations; determine, based at least in part on the predictive input, a plurality of attention-based encoding vectors for the predictive input, wherein each attention-based encoding vector of the plurality of attention-based encoding vectors relates a corresponding encoding designation of the plurality of encoding designations to a related subset of the predictive input; determine, based at least in part on the plurality of encoding probability values, predictive entity data associated with the predictive entity, and deficiency utility data associated with the plurality of encoding designations, an encoding deficiency prediction for the predictive input, wherein the encoding deficiency prediction indicates a deficient subset of the plurality of encoding designations as well as a deficiency utility value for each encoding designation in the deficient subset; and for each encoding designation in the deficient subset, perform a corresponding prediction-based action based at least in part on the deficiency utility value for the encoding designation and the attention-based encoding vector for the encoding designation.

In accordance with yet another aspect, an apparatus comprising at least one processor and at least one memory including computer program code is provided. In one embodiment, the at least one memory and the computer program code may be configured to, with the processor, cause the apparatus to: receive a predictive input associated with a predictive entity; determine, based at least in part on the predictive input, a plurality of encoding probability values for the predictive input, wherein each encoding probability value of the plurality of encoding probability values indicates an estimated encoding association of the predictive input with a corresponding encoding designation of a plurality of encoding designations; determine, based at least in part on the predictive input, a plurality of attention-based encoding vectors for the predictive input, wherein each attention-based encoding vector of the plurality of attention-based encoding vectors relates a corresponding encoding designation of the plurality of encoding designations to a related subset of the predictive input; determine, based at least in part on the plurality of encoding probability values, predictive entity data associated with the predictive entity, and deficiency utility data associated with the plurality of encoding designations, an encoding deficiency prediction for the predictive input, wherein the encoding deficiency prediction indicates a deficient subset of the plurality of encoding designations as well as a deficiency utility value for each encoding designation in the deficient subset; and for each encoding designation in the deficient subset, perform a corresponding prediction-based action based at least in part on the deficiency utility value for the encoding designation and the attention-based encoding vector for the encoding designation.

BRIEF DESCRIPTION OF THE DRAWINGS

Figure 1:
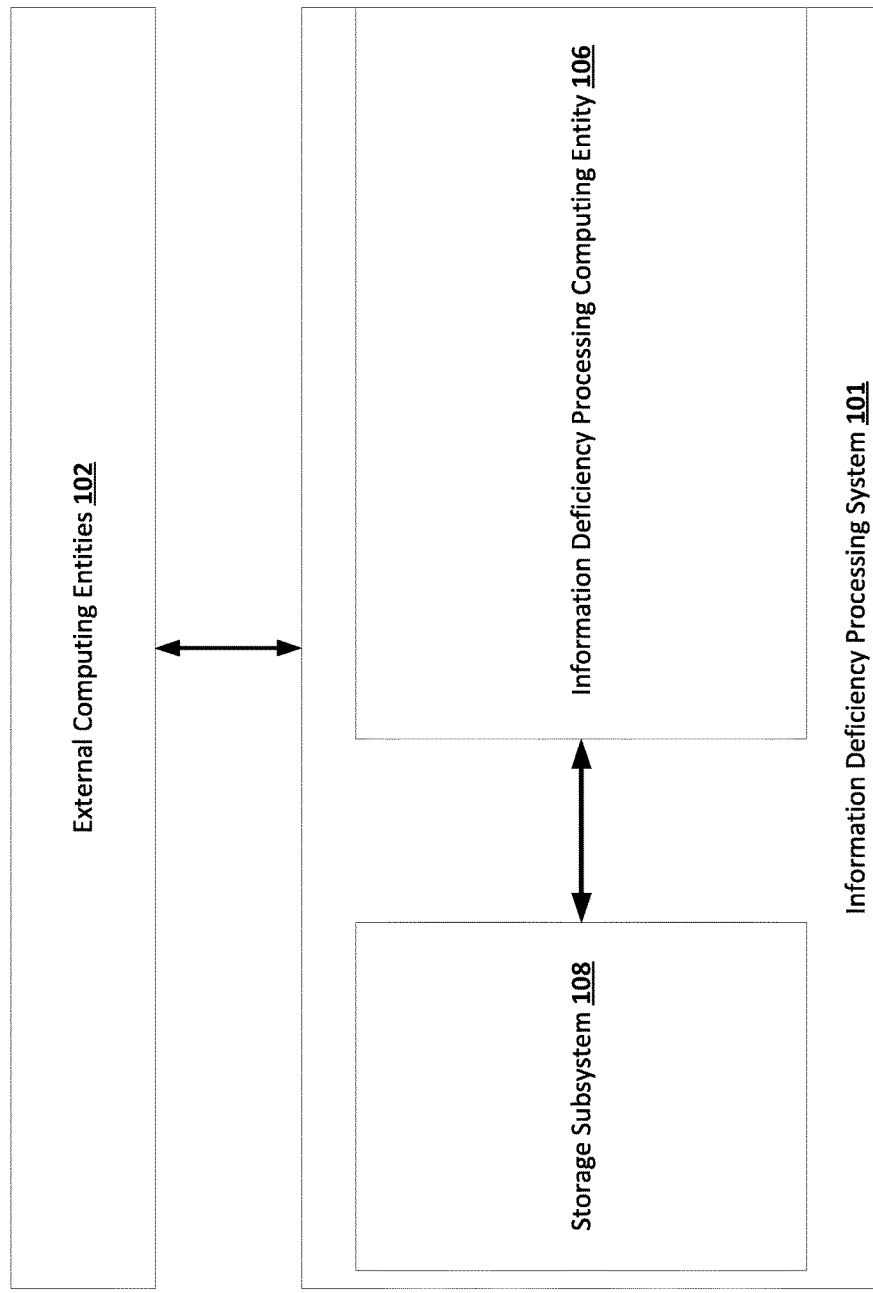

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
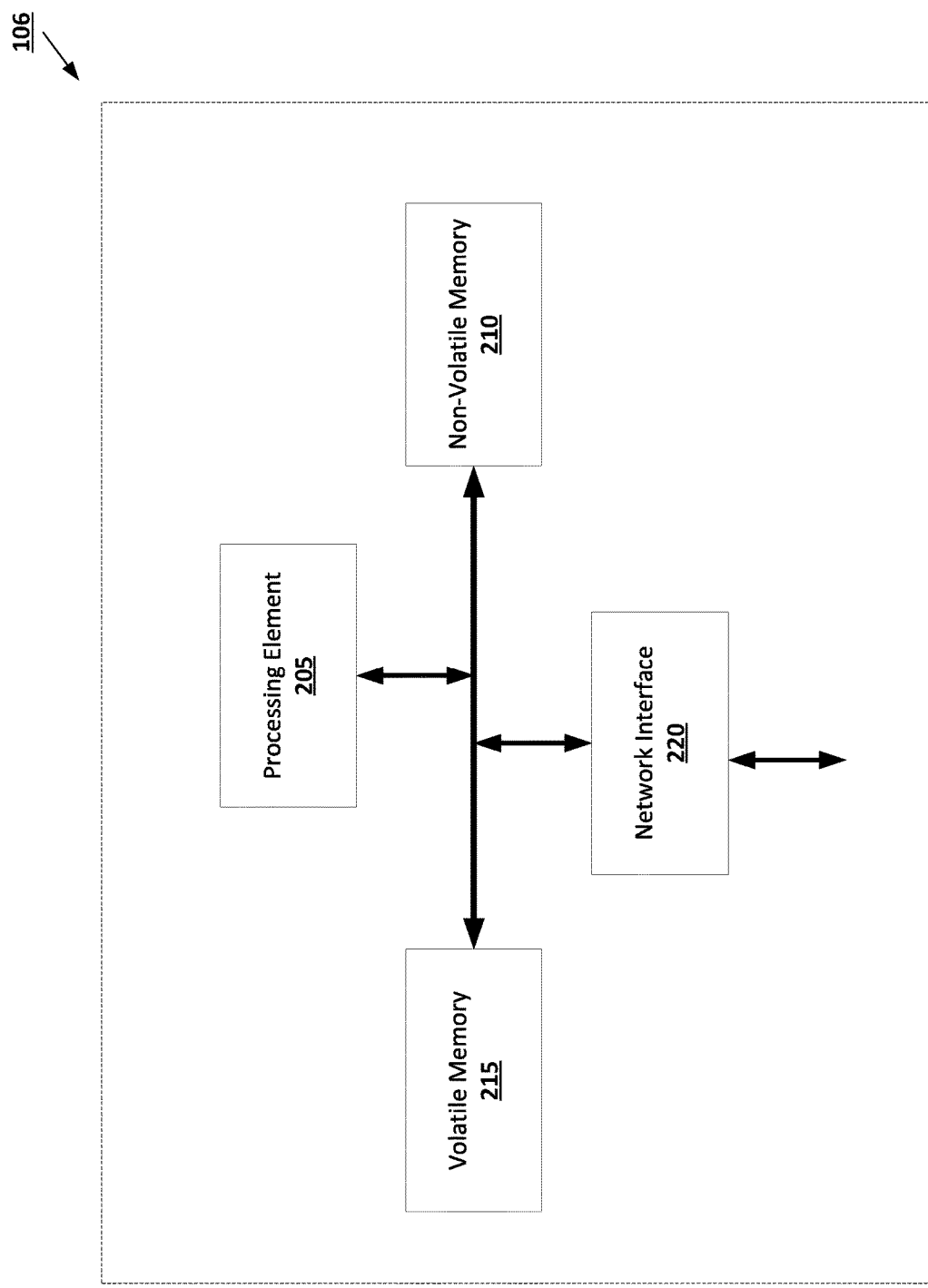

FIG. 2 provides an example information deficiency processing computing entity in accordance with some embodiments discussed herein.

Figure 3:
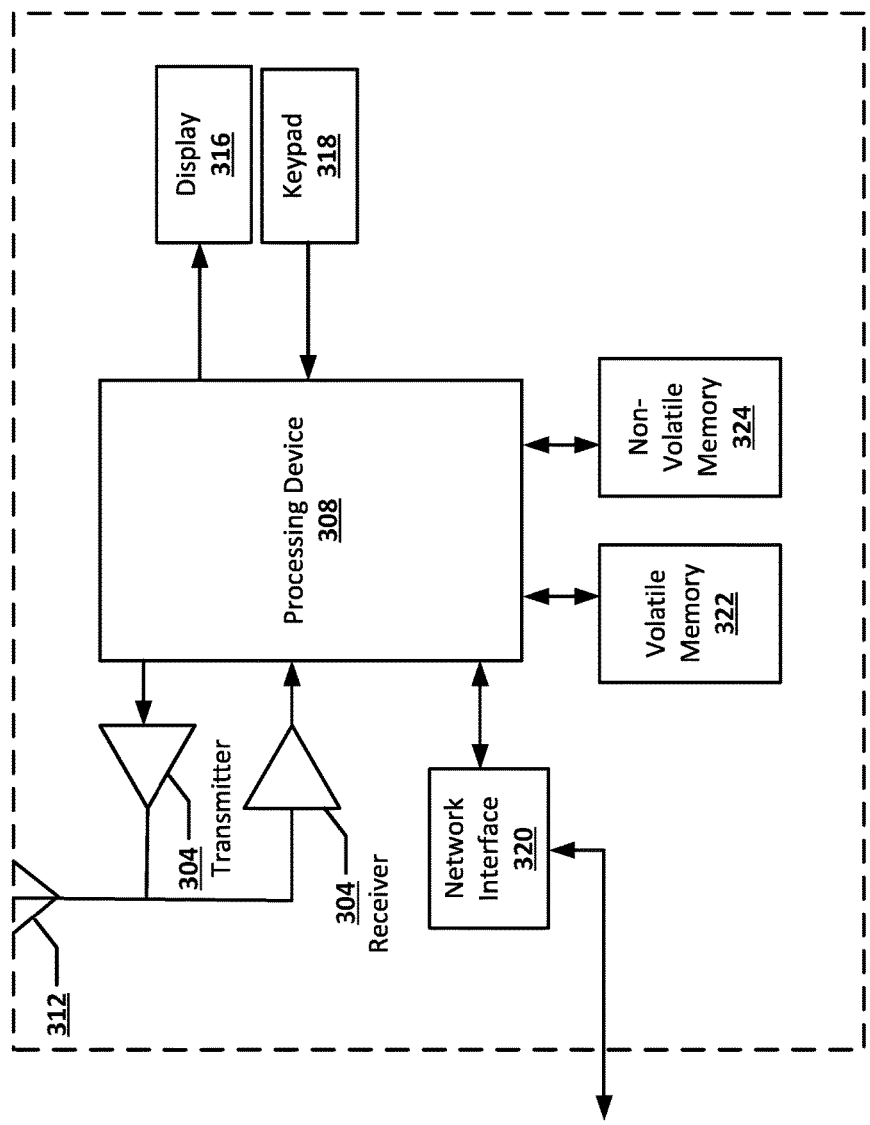

FIG. 3 provides an example external computing entity in accordance with some embodiments discussed herein.

Figure 4:
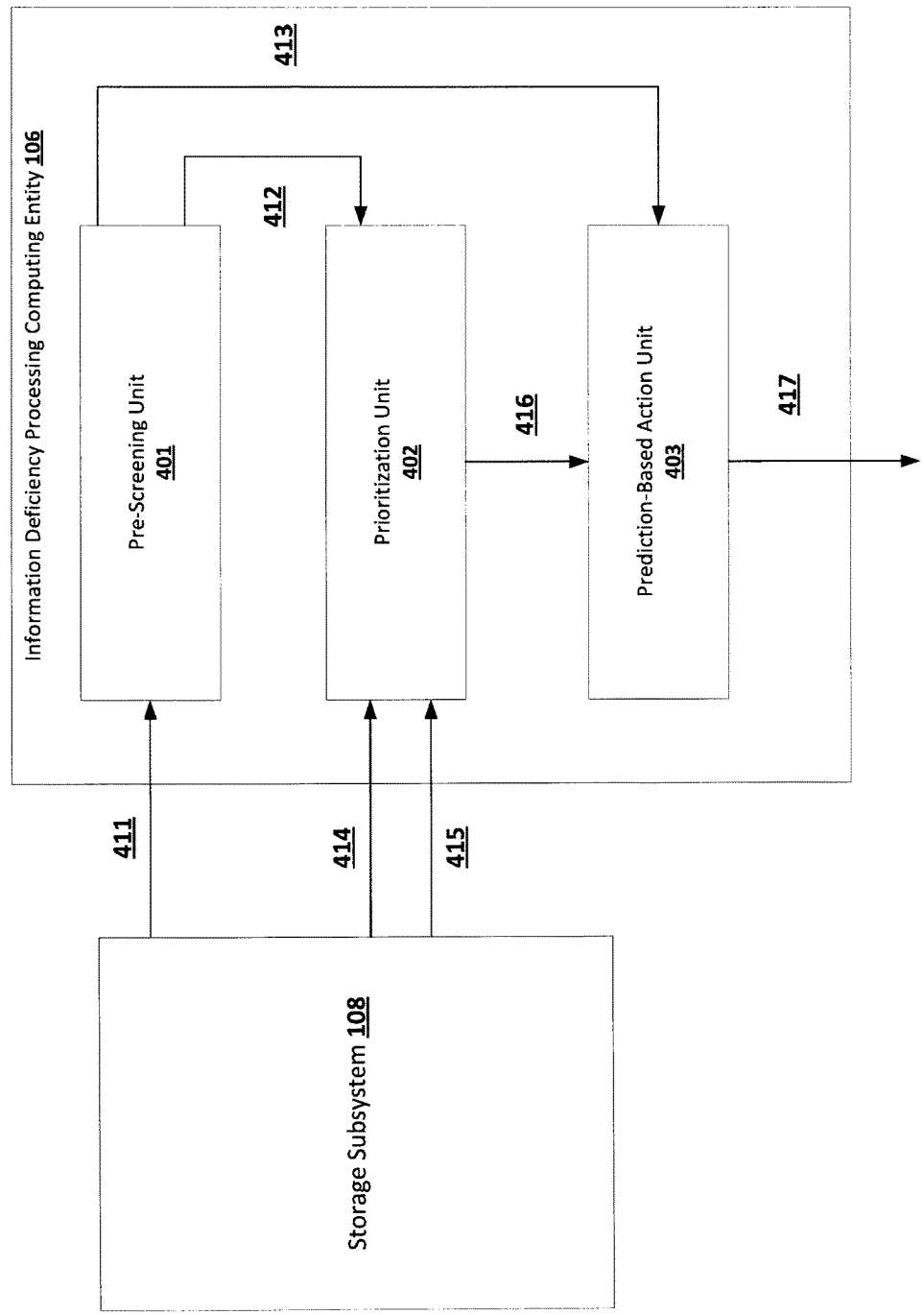

FIG. 4 is a flowchart diagram of an example process for performing label-based information deficiency processing in accordance with some embodiments discussed herein.

Figure 5:
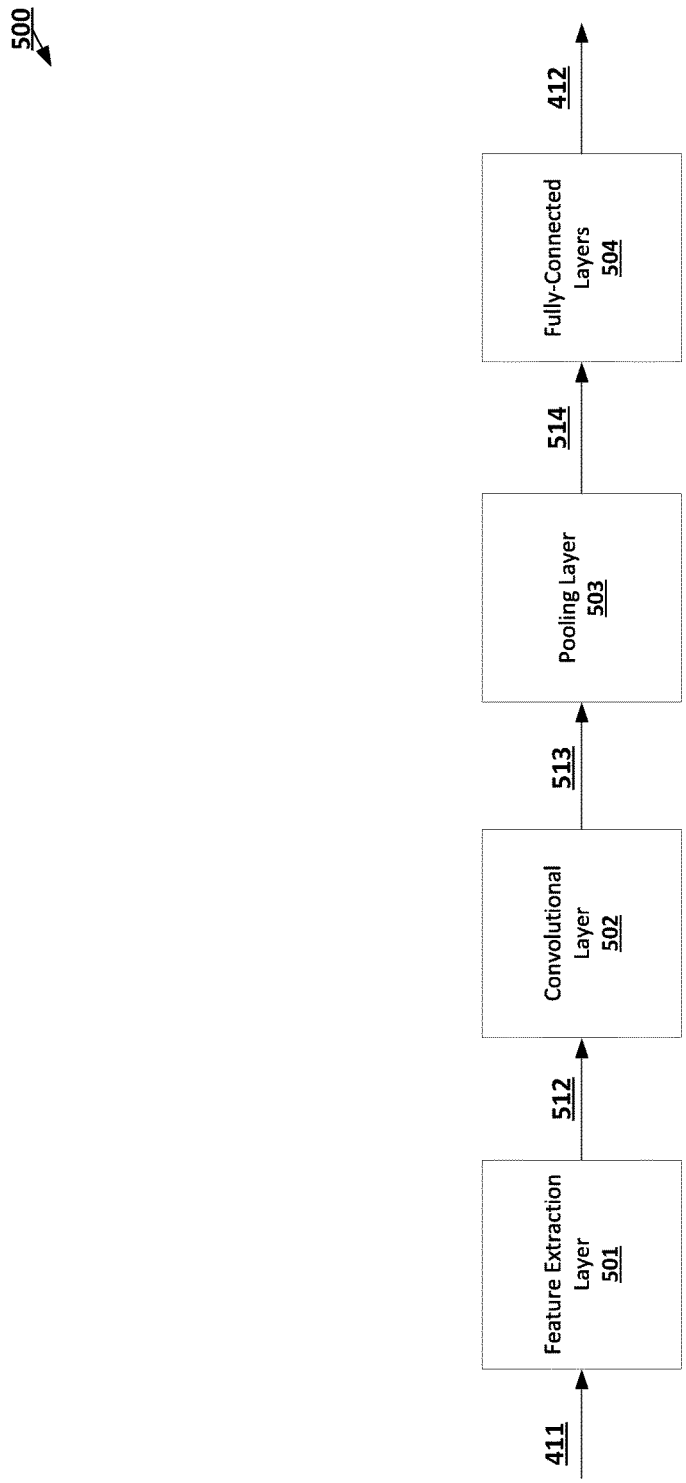

FIG. 5 provides an operational example of a multi-channel convolutional encoding machine learning model in accordance with some embodiments discussed herein.

Figure 6:
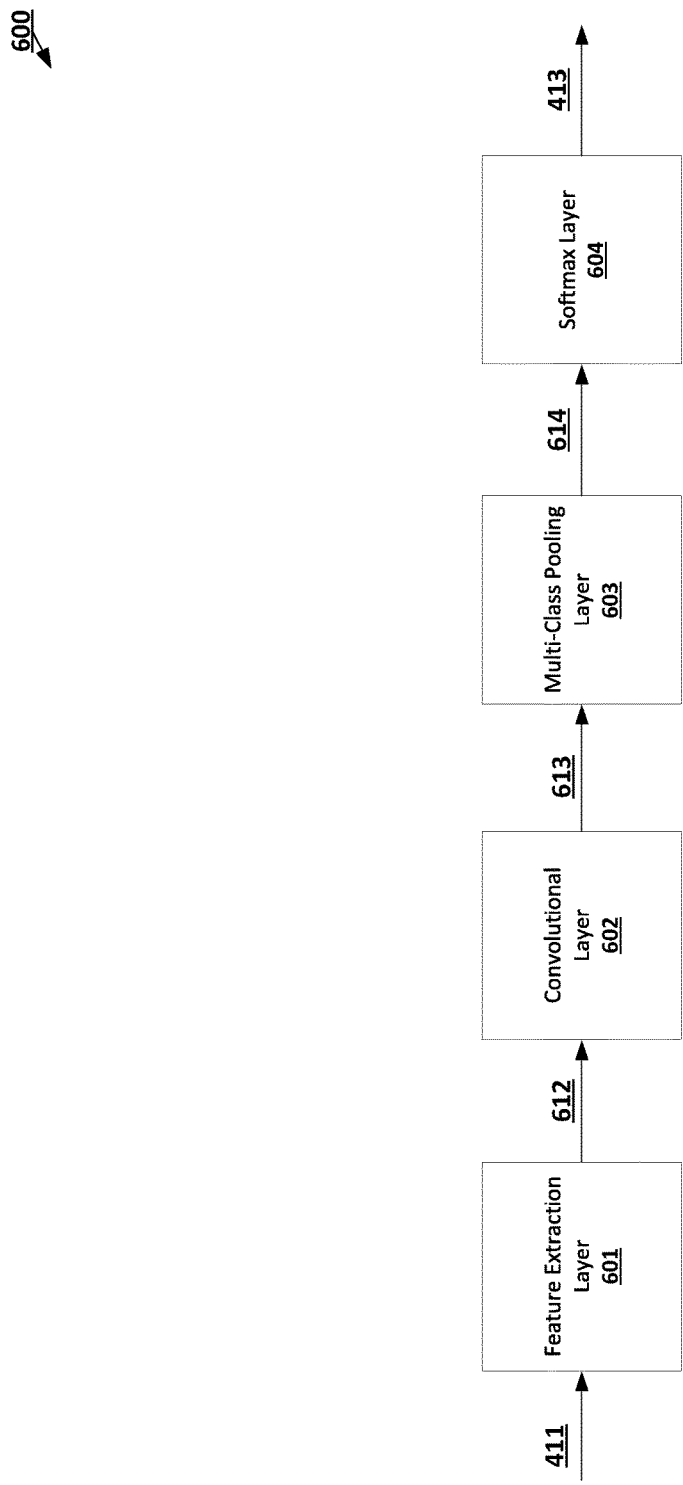

FIG. 6 provides an operational example of an attention-based machine learning model in accordance with some embodiments discussed herein.

Figure 7:
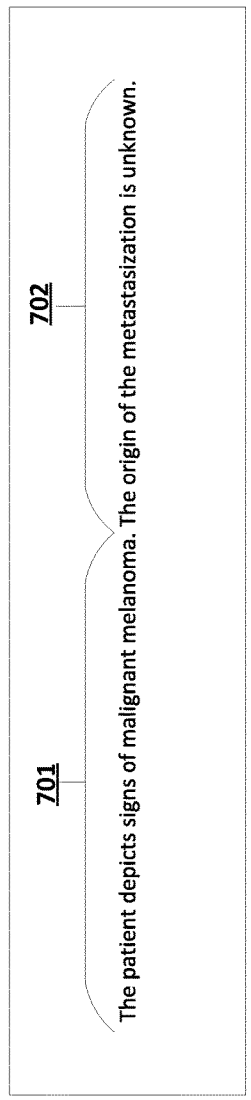

FIG. 7 provides an operational example of a multi-subsequence predictive input in accordance with some embodiments discussed herein.

Figure 8:
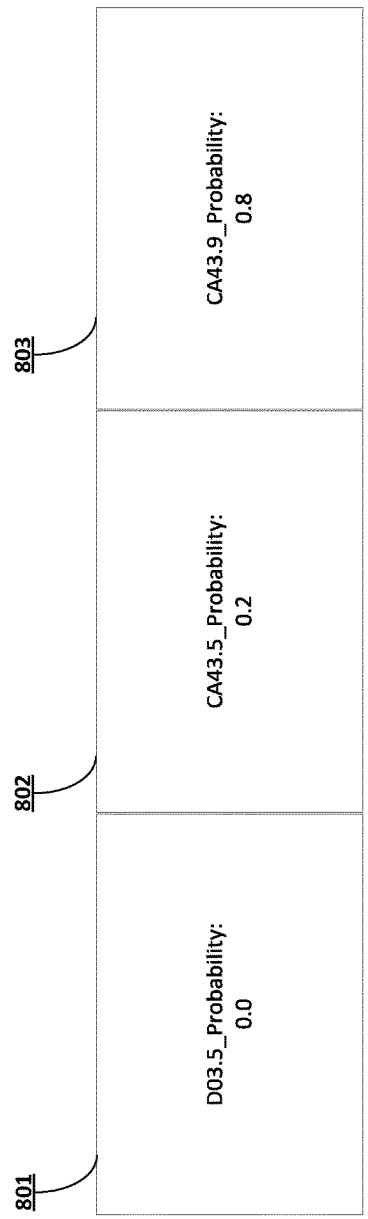

FIG. 8 provides an operational example of an encoding probability vector in accordance with some embodiments discussed herein.

Figure 9:
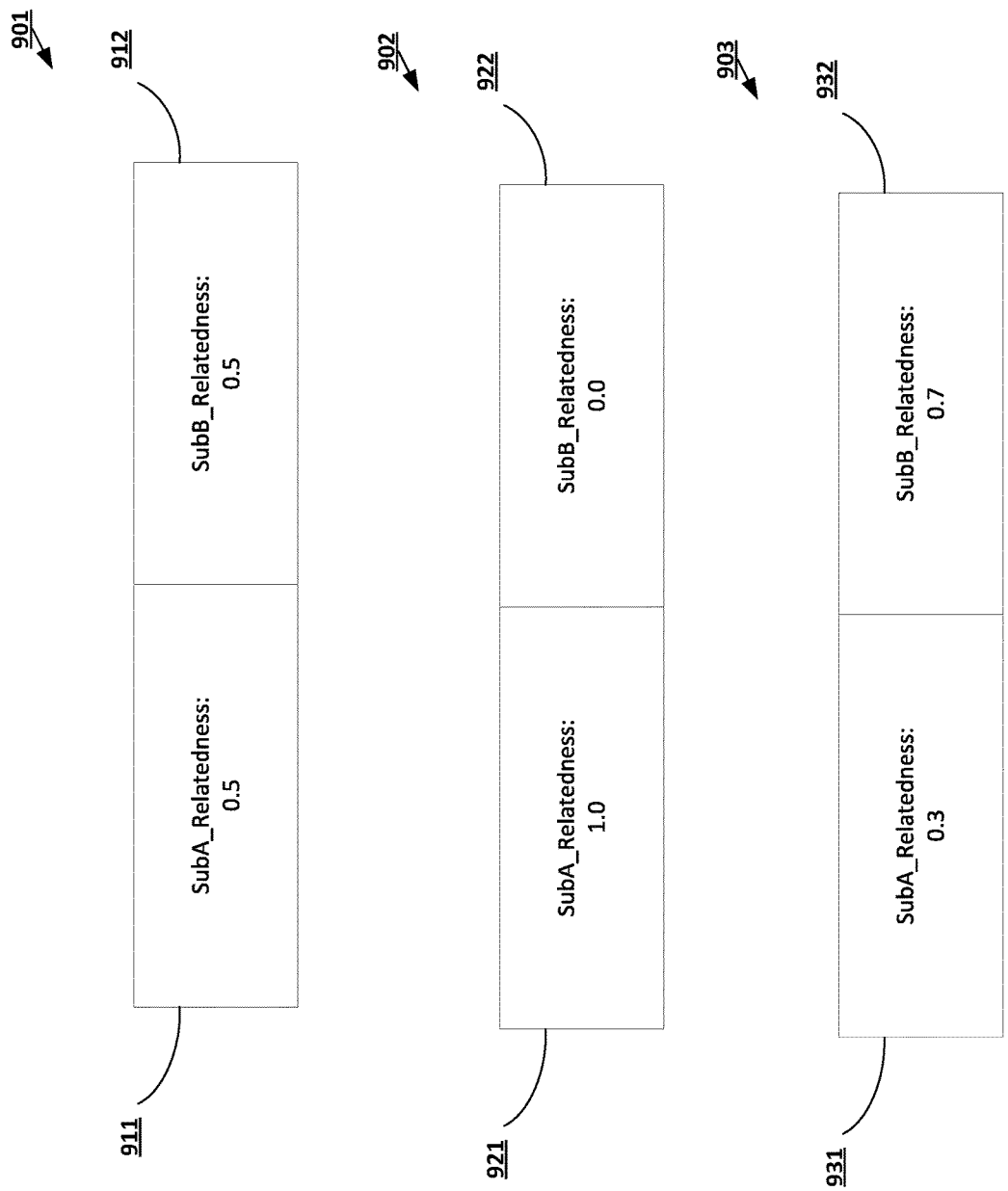

FIG. 9 provides operational examples of attention-based encoding vectors in accordance with some embodiments discussed herein.

Figure 10:
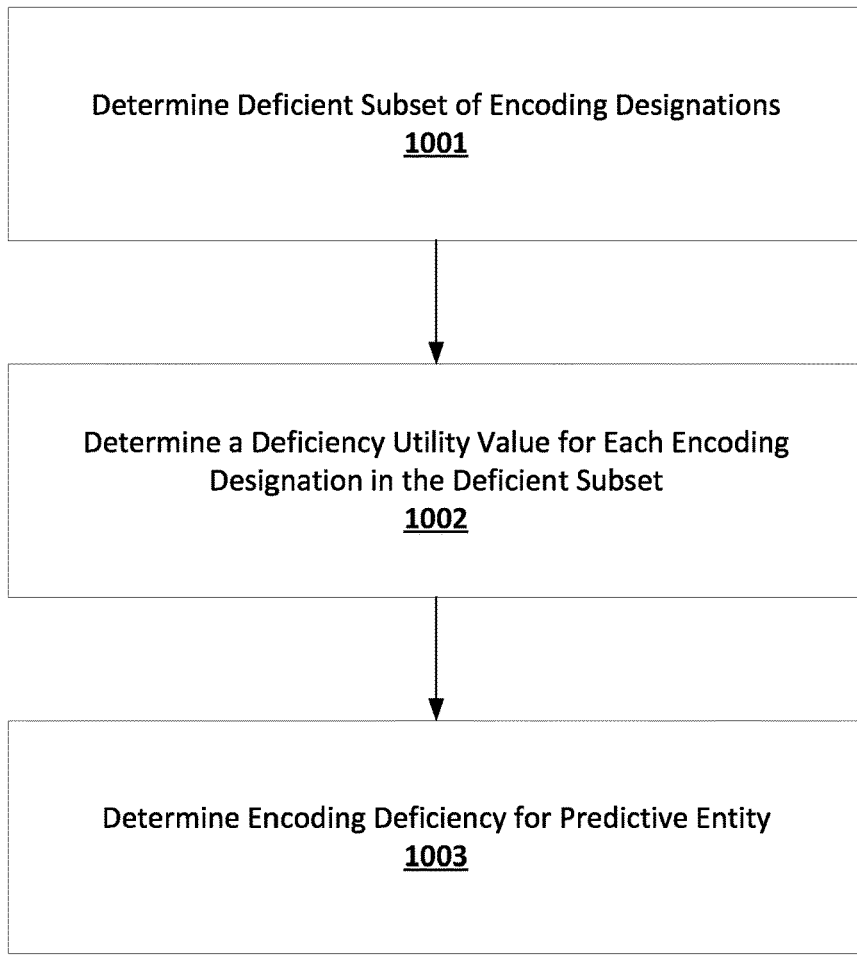

FIG. 10 is a flowchart diagram of an example process for generating an encoding deficiency prediction for a predictive entity in accordance with some embodiments discussed herein.

Figure 11:
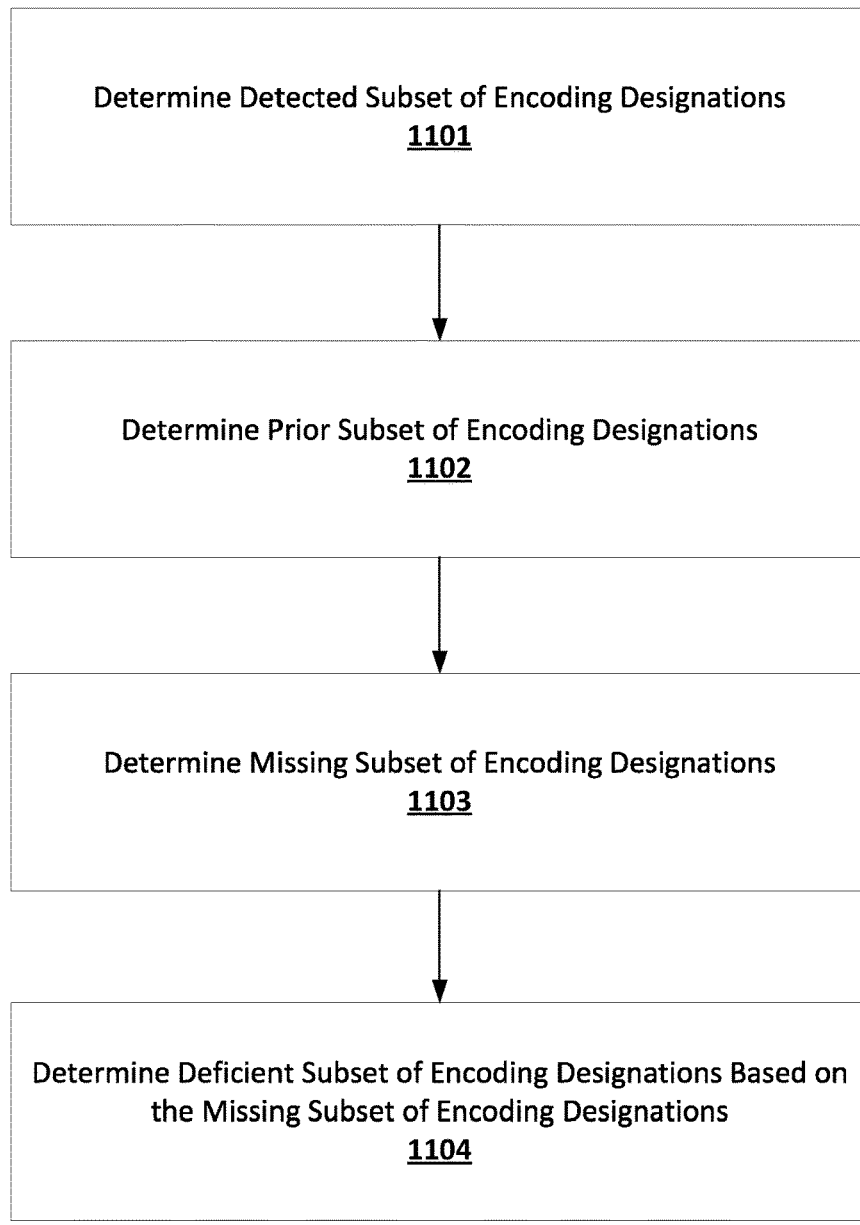

FIG. 11 is a flowchart diagram of an example process for determining a deficient subset of a group of encoding designations in accordance with some embodiments discussed herein.

Figure 12:
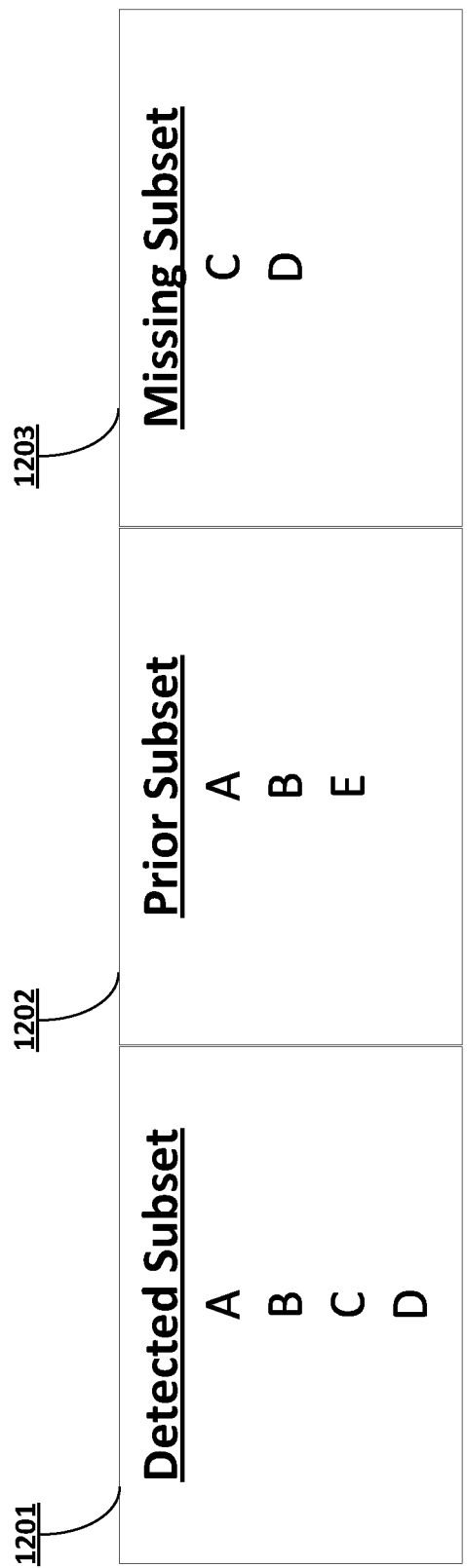

FIG. 12 is an operational example of generating a missing subset of encoding designations in accordance with some embodiments discussed herein.

Figure 13:
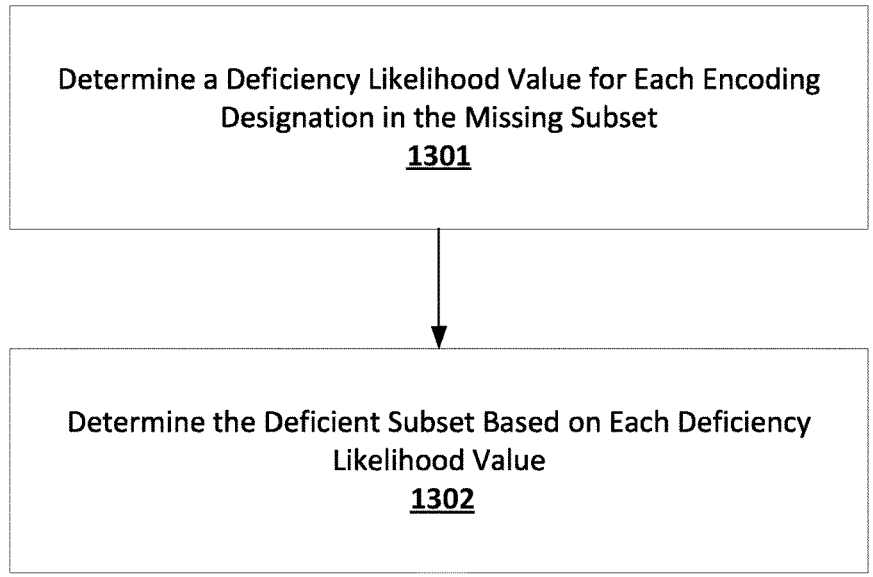

FIG. 13 is a flowchart diagram of an example process for determining a deficient subset of encoding designations based on a missing subset of encoding designations in accordance with some embodiments discussed herein.

FIG. 14 is an operational example of generating a natural language output for a responsive agent profile in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW

Various embodiments of the present invention address technical challenges associated with efficiency and reliability of label-based information deficiency processing. A label-based information deficiency processing task is a predictive task that seeks to identify information deficiencies about a predictive entity based on a predictive input associated with the noted predictive entity, where the predictive entity may potentially be associated with two or more labels selected from a pool of candidate encoding designations (e.g., two or more diagnosis codes selected from a pool of candidate diagnosis codes defined by a diagnosis code classification system). An example of a label-based information deficiency processing task is a task that includes identifying gaps in patient data based on comparing medical provider charts and underlying patient data, where the medical provider charts may potentially indicate presence of one or more diagnosis codes that are not indicated by patient data. In some embodiments, by comparing medical provider charts and underlying patient data, an information deficiency processing system can identify potential instances of superfluous procedures and/or inaccurate diagnoses and direct such instances to manual chart reviews in a prioritized manner.

To efficiency and reliably perform label-based information deficiency processing, an information deficiency processing system must perform a computationally costly label-based task followed by a computationally costly mapping of information deficiency predictions to prediction-based actions. The sequential combination of the two noted computationally costly tasks imposes substantial resource costs and reliability pressures on proposed label-based information deficiency processing systems. In some cases, developers of label-based information deficiency processing systems may be presented with tradeoffs between more resource-intensive accuracy of sequential processing and less resource-intensive inaccuracy of non-sequential processing.

To address the noted efficiency and reliability challenges associated with performing label-based information deficiency processing, various embodiments of the proposed invention utilize a pipeline with various inter-pipeline-stage dependencies to maintain the sequential structure while reducing the amount of per-pipeline-stage processing. For example, in accordance with one approach, a first stage of a label-based information deficiency processing pipeline generates encoding probability values and attention-based encoding vectors, a second stage of the label-based information deficiency processing pipeline utilizes the encoding probability values generated in the first stage of the label-based information deficiency processing pipeline to generate encoding deficiency predictions, and a third stage of the label-based information deficiency processing pipeline utilizes the attention-based encoding values generated in the first stage of the label-based information deficiency processing pipeline as well as encoding deficiency predictions generated in the second stage of the label-based information deficiency processing to identify and perform prediction-based actions to properly address information deficiencies.

By utilizing the pipeline-based techniques described herein, various embodiments of the present invention utilize various pipeline stages along with the various inter-pipeline-stage dependencies to maintain the sequential structure while reducing the amount of per-pipeline-stage processing. In doing so, various embodiments of the present invention are able to maintain reliability of a sequential approach to label-based information deficiency processing, while reducing computational costs of the noted sequential approach. This in turn enables various embodiments of the present invention to address technical challenges associated with efficiency and reliability of label-based information deficiency processing, make important contributions to improving efficiency and reliability of label-based information deficiency processing, and substantially improve efficiency and reliability of label-based information deficiency processing systems.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

FIG. 1 is a schematic diagram of an example architecture 100 for performing/executing label-based information deficiency processing. The architecture 100 includes an information deficiency processing system 101 configured to receive information deficiency processing requests (e.g., medical chart review requests) from one or more external computing entities 102, process the information deficiency processing requests to generate information deficiency processing outputs (e.g., medical chart review outputs), provide the information deficiency processing outputs to the external computing entities 102, and automatically perform prediction-based actions (e.g., cause performance of a manual medical chart review) in response to detecting information deficiency predictions in analyzed prediction inputs (e.g., medical chart data). An example of an information deficiency processing task is a medical chart review task.

In some embodiments, information deficiency processing system 101 may communicate with at least one of the external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The information deficiency processing system 101 may include an information deficiency processing computing entity 106 and a storage subsystem 108. The information deficiency processing computing entity 106 may be configured to receive information deficiency processing requests (e.g., medical chart review requests) from one or more external computing entities 102, process the information deficiency processing requests to generate information deficiency processing outputs (e.g., medical chart review outputs), provide the information deficiency processing outputs to the external computing entities 102, and automatically perform prediction-based actions (e.g., cause performance of a manual medical chart review) in response to detecting information deficiency predictions in analyzed prediction inputs (e.g., medical chart data).

The storage subsystem 108 may be configured to store input data used by the information deficiency processing computing entity 106 to perform information deficiency processing as well as model definition data for one or more machine learning models used by the information deficiency processing computing entity 106 to perform information deficiency processing. The storage subsystem 108 may further be configured to store configuration data associated with the information deficiency processing system 101, such as configuration data associated with the deficiency models maintained by the information deficiency processing system 101 and/or configuration data associated with the operation of the information deficiency processing computing entity 106.

The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Information Deficiency Processing

FIG. 2 provides a schematic of an information deficiency processing computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the information deficiency processing computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the information deficiency processing computing entity 106 may include or be in communication with one or more processing elements 205 (also referred to as processors, processing circuitry, and/or similar terms used herein interchangeably) that communicate with other elements within the information deficiency processing computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the information deficiency processing computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the information deficiency processing computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the information deficiency processing computing entity 106 with the assistance of the processing element 205 and operating system.

As indicated, in one embodiment, the information deficiency processing computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the information deficiency processing computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the information deficiency processing computing entity 106 may include or be in communication with one or more input elements, such as a keyboard input, a mouse input, a touch screen/display input, motion input, movement input, audio input, pointing device input, joystick input, keypad input, and/or the like. The information deficiency processing computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the information deficiency processing computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the information deficiency processing computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MIMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the information deficiency processing computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the information deficiency processing computing entity 106 and/or various other computing entities.

In another embodiment, the external computing entity 102 may include one or more components or functionality that are the same or similar to those of the information deficiency processing computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. EXEMPLARY SYSTEM OPERATIONS

FIG. 4 is a data flow diagram of an example process 400 for performing label-based information deficiency processing. Via the various steps/operations of process 400, the information deficiency processing computing entity the information deficiency processing computing entity 106 can classify predictive inputs (e.g., textual predictive inputs) based on a group of encoding designations selected from a large pool of candidate encoding designations, identify information deficiencies based on comparing the group of encoding designations and underlying predictive domain data, identify utility values for the identified information deficiencies, select prediction-based actions to correct the information deficiencies based on the identified utility values for the identified information deficiencies, and perform the selected prediction-based actions.

The process 400 begins when the pre-screening unit 401 of the information deficiency processing computing entity 106 retrieves a predictive input 411 (e.g., a predictive input 411 including text data) associated with a predictive entity from the storage subsystem 108. The predictive input 411 may be any collection of data utilized to detect encoding designations associated with the predictive entity. The predictive entity may be any real-world entity about which one or more predictive inferences may be performed. An example of a text input associated with a predictive entity is a collection of one or more medical charts (e.g., one or more medical provider charts) associated with a patient predictive entity. Although various embodiments of the present invention are described with reference to textual predictive entities, a person of ordinary skill in the art will recognize that predictive input data of one or more other data formats may similarly be utilized in addition to or instead of text input data to perform some or all of the innovative aspects of the label-based information deficiency processing concepts discussed herein.

In some embodiments, the pre-screening unit 401 may be configured to process the predictive input 411 to generate a plurality of encoding probability values 412 for the predictive entity. In some embodiments, each encoding probability value of the plurality of encoding probability values 412 indicates an estimated encoding association of the text input with a corresponding encoding designation of a plurality of encoding designations. In some embodiments, an encoding designation is a candidate classification of a particular predictive entity which can be selected individually or along with one or more other encoding designations as predicted classifications for the particular predictive input in a label-based predictive inference context. An example of a group of encoding designations is a group of medical diagnostic codes, such as at least a portion of the medical diagnostic codes identified by the 10th Revision of the International Statistical Classification of Diseases and Related Health Problems (ICD-10). In some embodiments, each encoding probability value for a particular medical diagnostic code indicates a likelihood that an underlying medical predictive input (e.g., a predictive input 411 generated based on one or more medical charts) associated with a predictive entity (e.g., a patient predictive entity) identifies that the medical diagnostic code may be applicable to a current medical condition of the predictive entity. In some embodiments, a label-based predictive inference is a predictive inference that seeks to predict information deficiencies about a predictive entity based on a predictive input associated with the noted predictive entity, where the predictive entity may potentially be associated with two or more labels selected from a pool of candidate encoding designations (e.g., two or more diagnosis codes selected from a pool of candidate diagnosis codes defined by a diagnosis code classification system)

In some embodiments, to generate the plurality of encoding probability values 412, the pre-screening unit 401 utilizes an encoding machine learning model, where the encoding machine learning model may be configured to process at least one of the predictive input 411, explanatory metadata associated with the predictive input 411, and provider metadata associated with the predictive input 411 to generate the plurality of encoding probability values 412. Explanatory metadata associated with the predictive input may include any data explaining the predictive input, such as human-generated data explaining some or all portions of a medical charts, human-generated data highlighting important portions of a medical chart, or automatically-generated data highlighting important portions of a medical chart. Provider metadata associated with the predictive input 411 may include date information associated with the predictive input 411, author information associated with the predictive input, provider information associated with the predictive input 411, and/or the like.

In some embodiments, the encoding machine learning model is a multi-channel convolutional neural network model characterized by a plurality of convolutional channels. In some of the noted embodiments, the plurality of convolutional channels include a static channel and a dynamic channel, where the static channel comprises a first vector generated based on the predictive input that is kept static during training of the encoding machine learning model, and the dynamic channel comprises a second vector generated based on the predictive input that changes during the training of the encoding machine learning model. In some embodiments, the multi-channel convolutional neural network model utilizes aspects of the multi-channel convolutional techniques described in Kim, *Convolutional Neural Networks for Sentence Classification*, arXiv:1408.5882v2 [cs.CL] 3 Sep. 2014, available online at https://arxiv.org/pdf/1408.5882.pdf.

An operational example of a multi-channel convolutional encoding machine learning model 500 is presented in FIG. 5. As depicted in FIG. 5, the multi-channel convolutional encoding machine learning model 500 includes a feature extraction layer 501 configured to receive the predictive input 411 and generate predictive features 512 based on the predictive input 411. In some embodiments, to generate the predictive features 512 based on the predictive input 411, the feature extraction layer 501 identifies at least some of the tokens (e.g., words) used in the predictive input 411 and generates a feature vector for each identified token. In some embodiments, to generate a feature vector for a word token, the feature extraction layer 501 utilizes a Word2Vec algorithm. The predictive features 512 include feature vectors of various channels, e.g., static feature vectors that are not modified during training and dynamic feature vectors that are modified during training.

As further depicted in FIG. 5, the multi-channel convolutional encoding machine learning model 500 includes a convolutional layer 502 configured to generate feature maps 513 based on the predictive features 512. In some embodiments, to generate the feature maps 513 based on the predictive features 512, the convolutional layer 502 identifies windows of feature vectors among the predictive features 512 and applies a convolutional operation (e.g., a non-linear operation, such as a hyperbolic tangent operation) to each window of feature vectors to generate a feature map 513 for the window of feature vectors. For example, to generate the feature maps 513 based on the predictive features 512, the convolutional layer 502 may identify windows of words in the predictive input 411, identify groups of feature vectors for each window of words, and process each group of feature vectors to generate a feature map 513 for the corresponding window of words.

As further depicted in FIG. 5, the multi-channel convolutional encoding machine learning model 500 includes a pooling layer 503 configured to generate aggregate features 514 based on the feature maps 513. In some embodiments, to generate aggregate features 514 based on the feature maps 513, the pooling layer 503 applies a max-over-time pooling operation to each feature map 513 to generate a group of pooling results for the feature map 513, identifies the maxim pooling result for each feature map 513, and determines the aggregate feature 514 for each feature map 513 based on the maximum pooling result for the feature map 513.

As further depicted in FIG. 5, the multi-channel convolutional encoding machine learning model 500 includes one or more fully-connected layers 504 configured to generate the encoding probability values 412 based on the aggregate features 514. In some embodiments, the fully-connected layers 504 are trained using a dropout training mechanism. In some embodiments, to implement the dropout training mechanism, a penultimate layer of the fully-connected layers 504 is trained in accordance with a constraint that is determined based on the L2 norms of weight vectors for the fully-connected layers 504. In some embodiments, to implement the dropout training mechanism, during training, the output of a penultimate layer of the fully-connected layers 504 is adjusted using a masking vector of Bernoulli random variables with a probability of one. In some embodiments, the final layer of the fully-connected layers 504 applies a softmax normalization operation.

Returning to FIG. 4, after generating the encoding probability values 412, the pre-screening unit 401 provides the generated encoding probability values 412 to a prioritization unit 402 of the information deficiency processing computing entity 106. Moreover, as further depicted in FIG. 4, the pre-screening unit 401 generates a plurality of attention-based encoding vectors 413 for the plurality of encoding designations, where the pre-screening unit 401 provides to the prediction-based action unit 403.

In some embodiments, each attention-based encoding vector 413 of the plurality of attention-based encoding vectors 413 relates a corresponding encoding designation of the plurality of encoding designations to a related subset of the predictive input 411. In some embodiments, each attention-based encoding vector 413 associated with a corresponding encoding designation is a vector including two or more vector values, where each vector value is associated with a related subset of the predictive input 411 (e.g., a related sentence of the predictive input 411), and where a vector value associated with a corresponding related subset of the predictive input 411 indicates a likelihood that the corresponding related subset of the predictive input 411 relates to the corresponding encoding designation that is associated with the attention-based encoding vector 413. In some embodiments, each attention-based encoding vector 413 associated with a corresponding encoding designation indicates a discrete distribution of the encoding designation over subsets of the predictive input 411, e.g., over subsequences of a textual predictive input 411.

In some embodiments, to generate the plurality of attention-based encoding vectors 413, the pre-screening unit 401 utilizes an attention-based machine learning model configured to generate a corresponding attention-based discrete distribution over the predictive input 411 for each encoding designation of the plurality of encoding designations. In some of those embodiments, to generate the plurality of attention-based encoding vectors 413, the pre-screening unit 401 determines the attention-based encoding vector 413 for each encoding designation based on the corresponding attention-based discrete distribution over for the encoding designation.

In some embodiments, the attention-based machine learning model is configured to process at least one of the predictive input 411, explanatory metadata associated with the predictive input 411, and provider metadata associated with the predictive input 411 to generate the plurality of attention-based encoding vectors 413. Explanatory metadata associated with the predictive input may include any data explaining the predictive input 411, such as human-generated data explaining some or all portions of a medical charts, human-generated data highlighting important portions of a medical chart, or automatically-generated data highlighting important portions of a medical chart. Provider metadata associated with the predictive input 411 may include date information associated with the predictive input 411, author information associated with the predictive input, provider information associated with the predictive input 411, and/or the like.

In some embodiments, the attention-based machine learning model is an attention-based convolutional model that applies a corresponding attention-based mechanism for each encoding designation of the plurality of encoding designations. In some embodiments, the attention-based machine learning model utilizes at least some of the techniques discussed in Mullenbach et al., *Explainable Prediction of Medical Codes from Clinical Text*, Proceedings of North American Chapter of the Association for Computational Linguistics: Human Language Technologies (NAACL-HLT) 2018, pp. 1101-1111, available at https://www.aclweb.org/anthology/N18-1100.pdf.

An operational example of an attention-based machine learning model 600 is presented in FIG. 6. As depicted in FIG. 6, the attention-based machine learning model 600 includes a feature extraction layer 601 configured to receive the predictive input 411 and generate predictive features 612 based on the predictive input 411. In some embodiments, to generate the predictive features 612 based on the predictive input 411, the feature extraction layer 601 identifies at least some of the tokens (e.g., words) used in the predictive input 411 and generates a feature vector for each identified token. In some embodiments, to generate a feature vector for a word token, the feature extraction layer 601 utilizes a Word2Vec algorithm. The predictive features 612 may include feature vectors of various channels, e.g., static feature vectors that are not modified during training and dynamic feature vectors that are modified during training.

As further depicted in FIG. 6, the attention-based machine learning model 600 includes a convolutional layer 602 configured to generate feature maps 613 based on the predictive features 612. In some embodiments, to generate the feature maps 613 based on the predictive features 612, the convolutional layer 602 identifies windows of feature vectors among the predictive features 612 and applies a convolutional operation (e.g., a non-linear operation, such as a hyperbolic tangent operation) to each window of feature vectors to generate a feature map 613 for the window of feature vectors. For example, to generate the feature maps 613 based on the predictive features 612, the convolutional layer 602 may identify windows of words in the predictive input 411, identify groups of feature vectors for each window of words, and process each group of feature vectors to generate a feature map 613 for the corresponding window of words.

As further depicted in FIG. 6, the attention-based machine learning model 600 includes a multi-class pooling layer 603 configured to generate per-encoding feature maps 614 based on the feature maps 613. In some embodiments, to generate per-encoding feature maps 614 based on the feature maps 613, the multi-class pooling layer 603 is configured to apply a per-encoding pooling operation for each encoding designation to the feature map 613 for the encoding designation to generate a per-encoding feature value for the encoding designation. In some of those embodiments, subsequent to applying a per-encoding pooling operation for each encoding designation to the feature map 613 for the encoding designation to generate a per-encoding feature value for the encoding designation, the multi-class pooling layer 603 is configured to apply a per-encoding weight for each encoding designation to the per-encoding feature value for the encoding designation to generate the per-encoding feature map 614 for the encoding designation.

In some embodiments, to generate per-encoding feature maps 614 based on the previously-generated feature maps 613, the multi-class pooling layer 603 is configured to apply a per-encoding attention mechanism for each encoding designation to the feature map 613 for the encoding designation to generate a per-encoding feature value for the encoding designation. In some of those embodiments, subsequent to applying a per-encoding attention mechanism for each encoding designation to the feature map 613 for the encoding designation to generate a per-encoding feature value for the encoding designation, the multi-class pooling layer 603 is further configured to apply a per-encoding weight for each encoding designation to the per-encoding feature value for the encoding designation to generate the per-encoding feature map 614 for the encoding designation.

As further depicted in FIG. 6, the attention-based machine learning model 600 includes a softmax layer 604 configured to generate the plurality of attention-based encoding vectors 413 based on the plurality of per-encoding feature maps 614. In some embodiments, to generate the plurality of attention-based encoding vectors 413 based on the per-encoding feature maps 614, the softmax layer 604 applies a softmax normalization operation (or other normalization operation) to each per-encoding feature map 614 associated with an encoding designation in order to determine a distribution of the encoding designation over subsets of the predictive input 411.

An operational example of at least some of the steps/operations performed by the pre-screening unit 401 is presented in FIGS. 7-9. FIG. 7 depicts an example predictive input 700 including two subsequences: subsequence A 701 and subsequence B 702.

FIG. 8 depicts an example encoding probability vector 800 for the predictive input 700 that includes, as its first vector value 801, the encoding probability value for the predictive input 700 and a first encoding designation; as its second vector value 802, the encoding probability value for the predictive input 700 and a second encoding designation; and as its third vector value 803, the encoding probability value for the predictive input 700 and a third encoding designation.

FIG. 9 depicts three attention-based encoding vectors 901-903. As depicted in FIG. 9, the first vector value 911 of the attention-based encoding vector 901 indicates an estimated relevance of the subsequence A 701 of the predictive input 700 to the first encoding designation, while the second vector value 912 of the attention-based encoding vector 901 indicates an estimated relevance of the subsequence B 702 of the predictive input 700 to the first encoding designation. As further depicted in FIG. 9, the first vector value 921 of the attention-based encoding vector 902 indicates an estimated relevance of the subsequence A 701 of the predictive input 700 to the second encoding designation, while the second vector value 922 of the attention-based encoding vector 902 indicates an estimated relevance of the subsequence B 702 of the predictive input 700 to the second encoding designation. As further depicted in FIG. 9, the first vector value 931 of the attention-based encoding vector 903 indicates an estimated relevance of the subsequence A 701 of the predictive input 700 to the third encoding designation, while the second vector value 932 of the attention-based encoding vector 903 indicates an estimated relevance of the subsequence B 702 of the predictive input 700 to the third encoding designation.

In some embodiments, the pre-screening unit 401 includes one or more machine learning models. In some embodiments, at least one of the noted models (e.g., at least one of the encoding machine learning model and the attention-based machine learning model) is trained using a training method that pursues a dual optimization objective: maximizing prediction recall (e.g., encoding designation recall) for a fixed precision and minimizing the number of prediction-less inputs (e.g., medical charts with no encoding designation). In some embodiments, at least one of the noted models (e.g., at least one of the encoding machine learning model and the attention-based machine learning model) is trained in accordance with a tradeoff between precision and recall as well as a tradeoff between the above-noted two optimization objectives. To control both tradeoffs, the fixed precision can be defined by a user and can be adapted based on the findings from the feedback of responsive agent profiles and/or via separate evaluations using data provided by external agent profiles, which can be utilized to discover which encoding designations are still missing in the input data.

Returning to FIG. 4, the prioritization unit 402 of the information deficiency processing computing entity 106 is configured to receive the encoding probability values 412 from the pre-screening unit 401, retrieve predictive entity data 414 about the predictive entity from the storage subsystem 108, retrieve deficiency utility data 415 associated with the plurality of encoding designations from the storage subsystem 108, and process the received encoding probability values 412 in accordance with the predictive entity data 414 associated with the predictive entity and the deficiency utility data 415 associated with the plurality of encoding designations to generate an encoding deficiency prediction 416 for the predictive entity. In some embodiments, the encoding deficiency prediction 416 indicates a deficient subset of the plurality of encoding designations as well as a deficiency utility value for each encoding designation in the deficient subset.

In some embodiments, to generate the encoding deficiency prediction 416 for the predictive entity, the prioritization unit 402 performs the steps/operations depicted in FIG. 10, which is a flowchart diagram of an example process for generating an encoding deficiency prediction 416 for the predictive entity. As depicted in FIG. 10, the depicted process begins at step/operation 1001 when the prioritization unit 402 determines the deficient subset of the plurality of encoding deficiencies. In some embodiments, the prioritization unit 402 determines the deficient subset of the plurality of encoding deficiencies based on at least one of the plurality of encoding probability values 412, the predictive entity data 414 associated with the predictive entity, and the deficiency utility data 415 associated with the plurality of encoding designation.

In some embodiments, to determine the deficient subset of the plurality of encoding deficiencies, the prioritization unit 402 performs the steps/operations depicted in FIG. 11, which is a flowchart diagram of an example process for determining the deficient subset of the plurality of encoding deficiencies. The process depicted in FIG. 11 begins at step/operation 1101 when the prioritization unit 402 determines a detected subset of the plurality of encoding designations based on the plurality of encoding probability values 412. In some embodiments, the prioritization unit 402 determines that an encoding designation is in the detected subset of the plurality of encoding designations if the encoding probability value 412 for the encoding designation exceeds a universal encoding probability threshold for all of the encoding designations, where the universal encoding probability threshold may be determined based on a static threshold value, a dynamic threshold value, and/or a trained threshold value determined using an encoding probability threshold generation machine learning model. In some embodiments, the prioritization unit 402 determines that an encoding designation is in the detected subset of the plurality of encoding designations if the encoding probability value 412 for the encoding designation exceeds a per-designation encoding probability threshold for the encoding designation, where the per-designation encoding probability threshold may be determined based on a static threshold value, a dynamic threshold value, and/or a trained threshold value determined using an encoding probability threshold generation machine learning model.

At step/operation 1102, the prioritization unit 402 determines a prior subset of the plurality of encoding designations based on the predictive entity data 414 for the predictive entity. In some embodiments, the predictive entity data 414 indicate pre-existing encoding designations for the predictive entity. In some of those embodiments, the prior subset of the plurality of encoding designations are determined based on the pre-existing designations for the predictive entity. In some embodiments, the prioritization unit 402 determines that an encoding designation of the plurality of encoding designations is in the prior subset if the encoding designation is also indicated by the predictive entity data 414 for the predictive entity. Examples of predictive entity data 414 include patient documentation data for a patient predictive entity and patient history data for a patient predictive entity.

At step/operation 1103, the prioritization unit 402 determines a missing subset of the plurality of encoding designations based on the detected subset of the plurality of encoding designations and the prior subset of the plurality of encoding designations. In some embodiments, the prioritization unit 402 determines that an encoding designation is in the missing subset of encoding designations if the encoding designation is in the detected subset of the encoding designations but not in the prior subset of encoding designations. In some embodiments, the prioritization unit 402 determines that an encoding designation is in the missing subset of encoding designations if the encoding designation is in the detected subset of the encoding designations but the encoding designations is neither in the prior subset of encoding designations nor has a sufficiently related encoding designations in the prior subset of the encoding designation, where relatedness between encoding designations may be determined based on encoding designation similarity data determined in accordance with a multi-dimensional encoding designation similarity space. For example, as depicted in the operational example of FIG. 12, a missing encoding designation subset 1203 includes encoding designations C and D which are in the detected encoding designation subset 1201 but not in the prior encoding designation subset 1202.

At step/operation 1104, the prioritization unit 402 determines the deficient subset of encoding designations based on the missing subset of encoding designations. In some embodiments, the prioritization unit 402 determines that each encoding designation in the missing subset of encoding designations is also in the deficient subset of encoding designations. In some embodiments, to determine the deficient subset of encoding designations based on the missing subset of encoding designations, the prioritization unit 402 selects a subset of the missing subset of the encoding designations based on the likelihood that each encoding designation in the missing subset may be deficient. For example, the prioritization unit 402 may determine that each encoding designation in the missing subset of encoding designations is also in the deficient subset of encoding designations if the encoding designation has a deficiency likelihood that falls below a deficiency likelihood threshold, where the deficiency likelihood threshold may be determined based on a static threshold value, a dynamic threshold value, and/or a trained threshold value determined using a deficiency likelihood threshold generation machine learning model.

In some embodiments, to determine the deficient subset of encoding designations based on the missing subset of encoding designations, the prioritization unit 402 performs the steps/operations depicted in FIG. 13, which is an example process of determining a deficient subset of encoding designations based on a missing subset of encoding designations. As depicted in FIG. 13, the depicted process begins at step/operation 1301 when, the prioritization unit 402 determines, for each encoding designation in the missing subset, a designation deficiency likelihood value based on deficiency likelihood data associated with the plurality of encoding designations. In some embodiments, to determine a designation deficiency likelihood for an encoding designation in the missing subset, the prioritization unit 402 retrieves deficiency likelihood data associated with the encoding designation from the storage subsystem 108, where the deficiency likelihood data may indicate past rates of omissions of the encoding designations from predictive entity data 414.

At step/operation 1302, the prioritization unit 402 determines the deficient subset based on each designation deficiency likelihood value for an encoding designation in the missing subset. In some embodiments, the prioritization unit 402 determines that each encoding designation in the missing subset of encoding designations is also in the deficient subset of encoding designations if the encoding designation has a deficiency likelihood that falls below a deficiency likelihood threshold, where the deficiency likelihood threshold may be determined based on a static threshold value, a dynamic threshold value, and/or a trained threshold value determined using a deficiency likelihood threshold generation machine learning model.

Returning to FIG. 10, at step/operation 1002, the prioritization unit 402 determines, based on the deficiency utility data 415, each deficiency utility value for an encoding designation in the deficient subset. In some embodiments, the deficiency utility data 415 indicate an estimated utility cost and/or an estimated utility reward (e.g., an estimated financial cost and/or an estimated financial reward) associated with the deficiency of each encoding designation and/or each collection of one or more encoding designations. For example, the deficiency utility data 415 may indicate the likely financial cost of a gap of one or more corresponding encoding designations between patient documentation diagnosis codes and diagnosis codes determined based on a medical chart. This likely financial cost may be determined based on likely cost of medical operations and/or drug prescriptions likely associated with remedying the medical conditions identified by the missing diagnosis codes. In some embodiments, the deficiency utility value for an encoding designation in the deficient subset is an estimated utility cost and/or an estimated utility reward (e.g., an estimated financial cost and/or an estimated financial reward) associated with the deficiency of the encoding designation.

At step/operation 1103, the prioritization unit 402 determines the encoding deficiency prediction 416 for the predictive entity based on the deficient subset and each deficiency utility value for an encoding designation in the deficient subset. In some embodiments, to determine the encoding deficiency prediction 416 based on the deficient subset and each deficiency utility value for an encoding designation in the deficient subset, the prioritization unit 402 determines a priority value for each encoding designation in the deficient subset based on the deficiency utility value for the encoding designation in the deficient subset and generates the encoding deficiency prediction 416 as a data structure that includes, for each encoding designation in the deficient subset, an identifier of the encoding designation and the priority value for the encoding designation.

In some embodiments, to determine the priority value for an encoding designation in the deficient subset based on the deficiency utility value for the encoding designation in the deficient subset, the prioritization unit 402 maps the deficiency utility value for the encoding designation in the deficient subset to the priority value for an encoding designation in the deficient subset using a mapping function that is characterized by a positively increasing relationship between the priority value for the encoding designation in the deficient subset and the deficiency utility value for the encoding designation in the deficient subset.

Returning to FIG. 4, the prioritization unit 402 of the information deficiency processing computing entity 106 provides the encoding deficiency prediction 416 to the prediction-based action unit 403. Moreover, the prediction-based action unit 403 is configured to, for each encoding designation in the deficient subset, perform a corresponding prediction-based action 417 based on the deficiency utility value for the encoding designation 412 and the attention-based encoding vector 413 for the encoding designation.

A prediction-based action 417 is any automated and/or manual action performed to address deficiency of an encoding designation. In some embodiments, to perform a corresponding prediction-based action 417 for an encoding designation in the deficient subset, the prediction-based action unit 403 generates the corresponding prediction-based action 417 based on the deficiency utility value for the encoding designation 412 and the attention-based encoding vector 413 for the encoding designation. Other examples of prediction-based actions 417 may include automatic scheduling of appointments, automatic diagnoses, automatic diagnosis-related recommendations, automatic drug prescriptions, automatic medical provider notifications, automatic patient notifications, automatic medical provider load balancing operations, automatic medical provider server load balancing operations, automatic service call load balancing operations, and/or the like.

In some embodiments, to generate a corresponding prediction-based action 417 for an encoding designation in the deficient subset based on the deficiency utility value for the encoding designation 412 and the attention-based encoding vector 413 for the encoding designation, the prediction-based action unit 403 determines whether a responsive agent profile (e.g., a medical chart reviewer) should be allocated to the encoding designation in the deficient subset given the deficiency utility value of the encoding designation and the pool of available responsive agent profiles. In some embodiments, in response to determining that a responsive agent profile should be allocated to the encoding designation in the deficient subset given the deficiency utility value of the encoding designation and the pool of available responsive agent profiles, the prediction-based action unit 403 determines, based on encoding subject matter data for the encoding designation, a corresponding encoding subject matter for the encoding designation; selects a responsive agent profile for the encoding designation based on the corresponding subject matter for the encoding designation; generates one or more agent instructions for the responsive agent profile based on the attention-based encoding vector for the encoding designation; and provides the one or more agent instructions associated with the encoding designation to the corresponding subject matter.

In some embodiments, the one or more agent instructions for a responsive agent profile allocated to a particular encoding deficiency in the deficiency subset are presented as part of an assistance user interface, where the assistance user interface includes a natural language output for the encoding designation, and where the natural language output for an encoding designation may be generated based on the attention-based encoding vector 413 for the encoding designation. In some embodiments, to generate a natural language output for an encoding designation based on the attention-based encoding vector 413 for the encoding designation, the prediction-based action unit 403 maps the attention-based encoding vector 413 for the encoding designation to one or more natural language outputs for the encoding designation; generates an agent instruction interface that comprises the one or more natural language outputs; and presents the agent instruction interface to the responsive agent profile.

In some embodiments, to map the attention-based encoding vector 413 for an encoding designation to one or more natural language outputs for the encoding designation, the prediction-based action unit 403 determines an attention-based discrete distribution over for the encoding designation based on the attention-based encoding vector for the encoding designation, retrieves text generation modeling data configured to map attention-based discrete distributions to natural language outputs from the storage subsystem 108, and applies the text generation modeling data to the attention-based discrete distribution over for the encoding designation. An operational example of a natural language output 1400 for an encoding designation associated with a Chronic Obstructive Pulmonary Disease (COPD) encoding designation and an anticholinergics designation is presented in FIG. 14.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
receiving, by one or more processors, a predictive input associated with a predictive entity;
determining, by the one or more processors, based at least in part on the predictive input and using a first machine learning model comprising a multi-channel convolutional neural network model characterized by a plurality of convolutional channels, a plurality of encoding probability values for the predictive input, wherein each encoding probability value of the plurality of encoding probability values indicates an estimated encoding association of the predictive input with a corresponding encoding designation of a plurality of encoding designations;
determining, by the one or more processors, based at least in part on the predictive input and using a second machine learning model, a plurality of attention-based encoding vectors for the predictive input, wherein each attention-based encoding vector of the plurality of attention-based encoding vectors relate a corresponding encoding designation of the plurality of encoding designations to a related subset of the predictive input;
determining, by the one or more processors and based at least in part on (i) the plurality of encoding probability values, (ii) predictive entity data associated with the predictive entity, and (iii) deficiency utility data associated with the plurality of encoding designations, an encoding deficiency prediction for the predictive input, wherein (a) the encoding deficiency prediction indicates a deficient subset of the plurality of encoding designations and a deficiency utility value for one or more encoding designations in the deficient subset, and (b) the deficiency utility data indicate one or more of an estimated utility cost or an estimated utility reward associated with a deficiency of one or more encoding designations of the plurality of encoding designations; and
for the one or more encoding designations in the deficient subset, initiating, by the one or more processors, the performance of a corresponding prediction-based action based at least in part on the deficiency utility value and a corresponding attention-based encoding vector for the one or more encoding designations.

2. The computer-implemented method of claim 1, wherein determining the encoding deficiency prediction comprises:
determining, based at least in part on the plurality of encoding probability values and the predictive entity data, the deficient subset;
determining, based at least in part on the deficiency utility data, one or more deficiency utility values for the one or more encoding designations in the deficient subset; and
determining the encoding deficiency prediction based at least in part on the deficient subset and the one or more deficiency utility values for the one or more encoding designations in the deficient subset.

3. The computer-implemented method of claim 2, wherein determining the deficient subset comprises:
determining, based at least in part on the plurality of encoding probability values, a detected subset of the plurality of encoding designations;
determining, based at least in part on the predictive entity data, a prior subset of the plurality of encoding designations;
determining, based at least in part on the detected subset and the prior subset, a missing subset of the plurality of encoding designations; and
determining the deficient subset based at least in part on the missing subset.

4. The computer-implemented method of claim 3, wherein determining the deficient subset further comprises:
determining, for one or more encoding designations in the missing subset, one or more designation deficiency likelihood values based at least in part on deficiency likelihood data associated with the plurality of encoding designations; and
determining the deficient subset based at least in part on the one or more designation deficiency likelihood values for the one or more encoding designations in the missing subset.

5. The computer-implemented method of claim 1, wherein
the first machine learning model is configured to process the predictive input, explanatory metadata associated with the predictive input, and provider metadata associated with the predictive input to generate the plurality of encoding probability values.

6. The computer-implemented method of claim 5, wherein:
the plurality of convolutional channels include a static channel and a dynamic channel;
the static channel comprises a first vector generated based at least in part on the predictive input that is kept static during training of the first machine learning model; and
the dynamic channel comprises a second vector generated based at least in part on the predictive input that changes during the training of the first machine learning model.

7. The computer-implemented method of claim 1, wherein determining an attention-based encoding vector of the plurality of attention-based encoding vectors comprises:
generating, based at least in part on the predictive input, explanatory metadata associated with the predictive input, provider metadata associated with the predictive input, and the second machine learning model, a corresponding attention-based discrete distribution over the predictive input for one or more encoding designations of the plurality of encoding designations; and
for the one or more encoding designations of the plurality of encoding designations, determining the attention-based encoding vector based at least in part on the corresponding attention-based discrete distribution associated with the one or more encoding designations.

8. The computer-implemented method of claim 7, wherein the second machine learning model comprises an attention-based convolutional model that applies a corresponding attention-based mechanism for the one or more encoding designations of the plurality of encoding designations.

9. The computer-implemented method of claim 1, wherein:
the predictive input is associated with a medical chart;
the predictive entity is associated with a patient profile;

the predictive entity data associated with the patient profile comprise patient documentation data associated with the patient profile;

one or more encoding designations of the plurality of encoding designations are associated with a diagnosis code of a plurality of diagnosis codes; and the deficient subset is determined based at least in part on one or more diagnosis codes of the plurality of diagnosis codes that are extracted from the medical chart but that are not indicated by the patient documentation data.

10. The computer-implemented method of claim 1, wherein performing the corresponding prediction-based action for the one or more encoding designations in the deficient subset comprises:

determining, based at least in part on encoding subject matter data for the encoding designation, a corresponding encoding subject matter for the one or more encoding designations;

selecting a responsive agent profile for the one or more encoding designations based at least in part on the corresponding subject matter for the one or more encoding designations;

generating one or more agent instructions for the responsive agent profile based at least in part on the attention-based encoding vector for the one or more encoding designations; and providing the one or more agent instructions associated with the one or more encoding designations to the corresponding encoding subject matter.

11. The computer-implemented method of claim 10, wherein generating the one or more agent instructions comprises:

mapping an attention-based encoding vector for the one or more encoding designations to one or more natural language outputs for the one or more encoding designations;

generating an agent instruction interface that comprises the one or more natural language outputs; and presenting the agent instruction interface to the responsive agent profile.

12. An apparatus comprising one or more processors and at least one memory including program code, the at least one memory and the program code configured to, with the one or more processors, cause the apparatus to at least:

receive a predictive input associated with a predictive entity;

determine, based at least in part on the predictive input and using a first machine learning model comprising a multi-channel convolutional neural network model characterized by a plurality of convolutional channels, a plurality of encoding probability values for the predictive entity, wherein each encoding probability value of the plurality of encoding probability values indicates an estimated encoding association of the predictive input with a corresponding encoding designation of a plurality of encoding designations;

determine, based at least in part on the predictive input and using a second machine learning model, a plurality of attention-based encoding vectors, wherein each attention-based encoding vector of the plurality of attention-based encoding vectors relates a corresponding encoding designation of the plurality of encoding designations to a related subset of the predictive input;

determine, based at least in part on (i) the plurality of encoding probability values, (ii) predictive entity data associated with the predictive entity, and (iii) deficiency utility data associated with the plurality of encoding designations, an encoding deficiency prediction for the predictive input, wherein (a) the encoding deficiency prediction indicates a deficient subset of the plurality of encoding designations and a deficiency utility value for one or more encoding designations in the deficient subset, and (b) the deficiency utility data indicate one or more of an estimated utility cost or an estimated utility reward associated with a deficiency of one or more encoding designations of the plurality of encoding designations; and for the one or more encoding designations in the deficient subset, initiate the performance of a corresponding prediction-based action based at least in part on the deficiency utility value and a corresponding attention-based encoding vector for the one or more encoding designations.

13. The apparatus of claim 12, wherein determining the encoding deficiency prediction comprises:

determining, based at least in part on the plurality of encoding probability values and the predictive entity data, the deficient subset;

determining, based at least in part on the deficiency utility data, one or more deficiency utility values for the one or more encoding designations in the deficient subset; and determining the encoding deficiency prediction based at least in part on the deficient subset and the one or more deficiency utility values for the one or more encoding designations in the deficient subset.

14. The apparatus of claim 13, wherein determining the deficient subset comprises:

determining, based at least in part on the plurality of encoding probability values, a detected subset of the plurality of encoding designations;

determining, based at least in part on the predictive entity data, a prior subset of the plurality of encoding designations;

determining, based at least in part on the detected subset and the prior subset, a missing subset of the plurality of encoding designations; and determining the deficient subset based at least in part on the missing subset.

15. The apparatus of claim 12, wherein
the first machine learning model is configured to process the predictive input, explanatory metadata associated with the predictive input, and provider metadata associated with the predictive input to generate the plurality of encoding probability values.

16. The apparatus of claim 12, wherein determining an attention-based encoding vector of the plurality of attention-based encoding vectors comprises:

generating, based at least in part on the predictive input, explanatory metadata associated with the predictive input, provider metadata associated with the predictive input, and the second machine learning model, a corresponding attention-based discrete distribution over the predictive input for one or more encoding designations of the plurality of encoding designations; and for the one or more encoding designations of the plurality of encoding designations, determining the attention-based encoding vector based at least in part on the corresponding attention-based discrete distribution associated with the one or more encoding designations.

17. The apparatus of claim 12, wherein:
the predictive input is associated with a medical chart;
the predictive entity is associated with a patient profile;

the predictive entity data associated with the patient profile comprise patient documentation data associated with the patient profile;

one or more encoding designations of the plurality of encoding designations are associated with a diagnosis code of a plurality of diagnosis codes; and the deficient subset is determined based at least in part on one or more diagnosis codes of the plurality of diagnosis codes that are extracted from the medical chart but that are not indicated by the patient documentation data.

18. The apparatus of claim 12, wherein performing the corresponding prediction-based action for the one or more encoding designations in the deficient subset comprises:

determining, based at least in part on encoding subject matter data for the one or more encoding designations, a corresponding encoding subject matter for the one or more encoding designations;

selecting a responsive agent profile for the one or more encoding designations based at least in part on the corresponding subject matter for the one or more encoding designations;

generating one or more agent instructions for the responsive agent profile based at least in part on the attention-based encoding vector for the one or more encoding designations; and providing the one or more agent instructions associated with the one or more encoding designations to the corresponding encoding subject matter.

19. The apparatus of claim 18, wherein generating the one or more agent instructions comprises:

mapping an attention-based encoding vector for the one or more encoding designations to one or more natural language outputs for the one or more encoding designations;

generating an agent instruction interface that comprises the one or more natural language outputs; and presenting the agent instruction interface to the responsive agent profile.

20. At least one non-transitory computer-readable storage medium having computer-readable program code portions stored therein, the computer-readable program code portions configured, when executed by one or more processors, to:

receive a predictive input associated with a predictive entity;

determine, based at least in part on the predictive input and using a first machine learning model comprising a multi-channel convolutional neural network model characterized by a plurality of convolutional channels, a plurality of encoding probability values for the predictive entity, wherein each encoding probability value of the plurality of encoding probability values indicates an estimated encoding association of the predictive input with a corresponding encoding designation of a plurality of encoding designations;

determine, based at least in part on the predictive input and using a second machine learning model, a plurality of attention-based encoding vectors, wherein each attention-based encoding vector of the plurality of attention-based encoding vectors relates a corresponding encoding designation of the plurality of encoding designations to a related subset of the predictive input;

determine, based at least in part on (i) the plurality of encoding probability values, (ii) predictive entity data associated with the predictive entity, and (iii) deficiency utility data associated with the plurality of encoding designations, an encoding deficiency prediction for the predictive input, wherein (a) the encoding deficiency prediction indicates a deficient subset of the plurality of encoding designations and a deficiency utility value for one or more encoding designations in the deficient subset, and (b) the deficiency utility data indicate one or more of an estimated utility cost or an estimated utility reward associated with a deficiency of one or more encoding designations of the plurality of encoding designations; and for the one or more encoding designations in the deficient subset, initiate the performance of corresponding prediction-based action based at least in part on the deficiency utility value and a corresponding attention-based encoding vector for the one or more encoding designations.

* * * * *

UNITED STATES PATENT AND TRADEMARK OFFICE
CERTIFICATE OF CORRECTION

| | | |
|---|---|---|
| PATENT NO. | : 11,783,225 B2 | Page 1 of 1 |
| APPLICATION NO. | : 16/747686 | |
| DATED | : October 10, 2023 | |
| INVENTOR(S) | : Donald W. James et al. | |

It is certified that error appears in the above-identified patent and that said Letters Patent is hereby corrected as shown below:

In the Claims

In Column 28, Line 36, Claim 20, delete "of" and insert -- of a --, therefor.

Signed and Sealed this
Thirtieth Day of January, 2024

Katherine Kelly Vidal
*Director of the United States Patent and Trademark Office*